United States Patent [19]

Tani et al.

[11] Patent Number: 5,126,329
[45] Date of Patent: Jun. 30, 1992

[54] GLUCOSAMINE DERIVATIVES AND COMPOSITIONS REAGENTS AND CONTAINING THE SAME

[75] Inventors: Kenji Tani; Yoshio Nakamura, both of Koriyama; Takeshi Nagasawa, Urawa, all of Japan

[73] Assignee: Nitto Boseki Co., Ltd., Fukushima, Japan

[21] Appl. No.: 457,266

[22] Filed: Dec. 27, 1989

[30] Foreign Application Priority Data

Dec. 29, 1988 [JP] Japan .................. 63-331646

[51] Int. Cl.$^5$ .......................... C07H 5/04; C07H 5/20
[52] U.S. Cl. ..................... 514/25; 536/17.2; 536/17.4; 536/18.1; 536/118
[58] Field of Search ............... 536/18.1, 17.4, 118; 514/25

Primary Examiner—Johnnie R. Brown
Assistant Examiner—Aleya Rahman

[57] ABSTRACT

Novel phenylazonaphthol derivatives, e.g., 4-(4'-nitro-2'-sulfophenylazo)-1-naphthyl-N-acetyl-β-D-glucosaminide sodium salt, are excellent substrates for determining N-acetyl-β-D-glucosaminidase (NAG) activity in urine collected from the patient with renal disorders. The substrate has high water solubility, is not affected by interferences in urine and provides a simple method for determination of NAG activity which is suited for both rate and endpoint assays.

8 Claims, 2 Drawing Sheets

GLUCOSAMINE DERIVATIVES AND COMPOSITIONS REAGENTS AND CONTAINING THE SAME

BACKGROUND OF THE INVENTION

1. FIELD OF THE INVENTION

The present invention relates to novel phenylazonapthyl-N-acetyl-β-D-glucosaminide derivatives, reagents for determination of N-acetyl-β-D-glucosaminidase activity and a method for determination of N-acetyl-β-D-glucosaminidase activity.

N-Acetyl-β-D-glucosaminidase is one of glycolytic enzymes and widely distributed in vital tissues, especially rich in the kidney. A high N-acetyl-β-D-glucosaminidase activity is noted particularly around the proximal convoluted kidney tubule.

Determination of N-acetyl-β-D-glucosaminidase activity is of clinically great significance as giving useful information for early diagnosis of denial reaction after renal transplantation, diagnosis and course observation of various diseases such as acute renal insufficiency, glomerulonephritis, etc., renal toxicity with drug, and the like.

For determination of N-acetyl-β-D-glucosaminidase (hereafter often simply referred to as NAG) activity, it is conventional to react NAG on a substrate obtained by binding p-nitrophenol to N-acetyl-β-D-glucosamine at the reducing end thereof and perform colorimetry of p-nitrophenol released [Methods Engymol., 28. 702 (1972) and Biochem. J., 78. 106 (1961)].

In this method, however, it is necessary to determine urine blank. In addition, a molecular extinction coefficient of a colored substance is relatively small so that the method involves a defect that a reaction should be carried out over long periods of time to enhance analysis sensitivity.

A method using a substrate obtained by binding 4-methylumbelliferone to N-acetylglucosamine [Clin. Chim. Acta, 24. 189 (1969)]is also used. However, the methods encounter problems that since the reaction is carried out at a substrate concentration lower than Km value due to poor solubility of the substrate, the method tends to be affected by interferents in urine and urine blank must be measured as in the method using p-nitrophenol.

As an improved substrate for requiring no blank test, there is known m-cresolsulfophthalyl N-acetyl-β-D-glucosaminide (Japanese Patent Application KOKAI (Laid-Open) No. 58-994 and Japanese Patent Application KOKOKU (published for purpose of opposition) No. 63-7196). However, since these methods are directed to endpoint assay which comprises adding a reagent for terminating the reaction and forming a color in an alkaline region, the methods involve drawbacks that the assay should be performed using two reagents and it takes a long time and therefore, type of machines used for automated operations is limited, and the like.

In order to eliminate the drawbacks in the known methods, there has been proposed a rate assay for determining a difference in absorbance of NAG activity with passage of time in a definite time period during which the enzyme reaction proceeds. As substrates applicable to such rate assay, there are known 2-chloro-4-nitrophenyl-N-acetyl-β-D-glucosaminide 4-chloro-2-nitrophenyl-N-acetyl-β-D-glucosaminide (Japanese Patent Application Laid-Open No. 61-112092). However, solubility of the substrate is poor and the reaction is carried out at a substrate concentration lower than Km value. Since the method tends to be affected by interferents in urine and the assay is made at a wavelength of 405 nm, it is troublesome in that urine blank must be measured as in the method using p-nitrophenol.

In colorimetry, urine blank is measured to eliminate interference caused mainly by billirubin and hemoglobin. In order to omit the urine blank measurement, it is necessary that a wavelength for the measurement be set in a region longer than 540 nm which is free of interference by these substances.

As a result of various investigations to solve these problems, the present inventors have succeeded in accurately determining NAG activity in a sample in a simple manner using a solution containing a phenylazonapht hyl-N-acetyl-β-D-glucosaminide derivative as substrate.

SUMMARY OF THE INVENTION

A first aspect of the present invention relates to novel phenylazonaphthyl-N-acetyl-β-D-glucosaminide derivatives represented by general formula [I]:

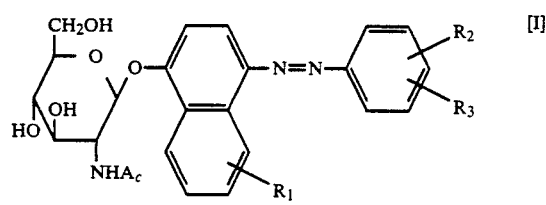

wherein at least one of $R_1$ through $R_3$ represents a sulfonic acid group or an alkali metal sulfonate group and the balance represents a halogen atom, methoxy group, nitro group or hydrogen atom.

A second aspect of the present invention relates to reagents for determining N-acetyl-β-D-glucosaminidase activity containing as substrate phenylazonaphthyl-N-acetyl-β-D-glucosaminde derivatives represented by general formula [I] described above.

A third aspect of the present invention relates to a method for colorimetric determination of N-acetyl-β-D-glucosaminidase activity which comprises dissolving reagents containing novel phenylazonaphthyl-N-acetyl-β-D-glucosaminide derivatives shown by general formula [I] described above in a buffer solution, adding a sample to the solution to incubate, and allowing the produced phenylazonaphthol derivatives to form a color with an alkali solution.

DETAILED DESCRIPTION OF PREFERRED EMBODIMENTS

The substrate used for determination of NAG activity according to the present invention is represented by general formula [I] described above, that is, compounds in which N-acetylglucosamine is bound to substituted aromatic compounds through β-bond at the reducing end thereof.

Examples of the alkali metal sulfonate group in general formula [I] include sodium sulfonate, potassium sulfonate, etc. As the halogen atom, there are fluorine, chlorine, bromine, etc.

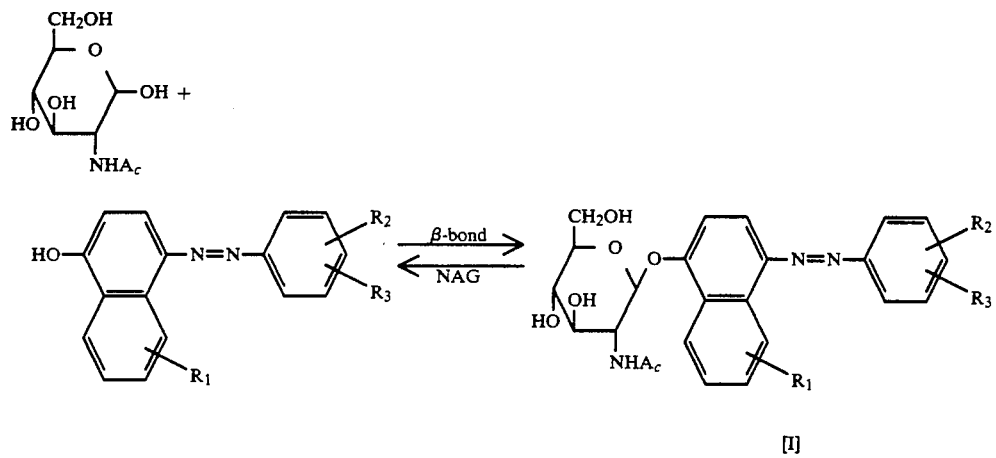

[I]

(wherein at least one of $R_1$ through $R_3$ represents a sulfonic acid group or an alkali metal sulfonate group and the balance represents a halogen atom, methoxy group, nitro group or hydrogen atom.)

The substituted aromatic compounds described above correspond to algycons produced by reacting NAG with the compounds of general formula [I] as its substrate and cleaving the substrate. The substituted aromatic compounds show spectral absorption which is different from that of the substrate.

The aglycons which are produced by cleavage of the substrate are phenylazonaphthol derivatives represented by the following general formula [II]:

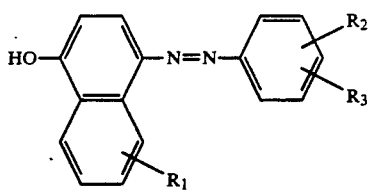

wherein $R_1$ through $R_3$ have the same significances as described above.

Examples of the phenylazonaphthol derivatives are 4-phenylazo-1-naphthol-4'-sulfonic acid, 4-phenylazo-1-naphthol-4'-nitro-2'-sulfonic acid, 4-(4'-methoxyphenylazo)-1-naphthol-5-sulfonic acid, 4-(2'-chloro-4'-nitrophenylazo)-1-naphthol-5-sulfonic acid, etc. and alkali metal salts thereof.

Figure 1:
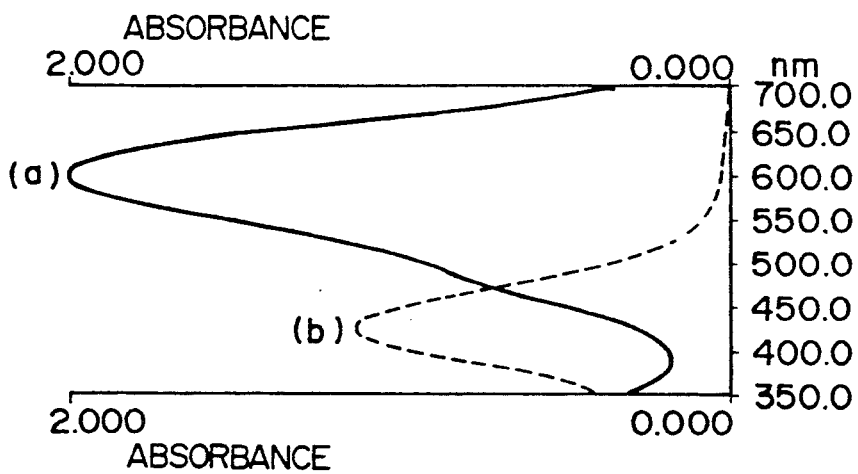
FIG. 1 shows UV spectra of (a) sodium 4-phenylazo-1-naphthol-4'-nitro-2'-sulfonate and (b) 4-(4'-nitro-2'-sulfonphenylazo)-1-naphthyl-N-acetyl-β-D-glucosaminide sodium salt.
Figure 2:
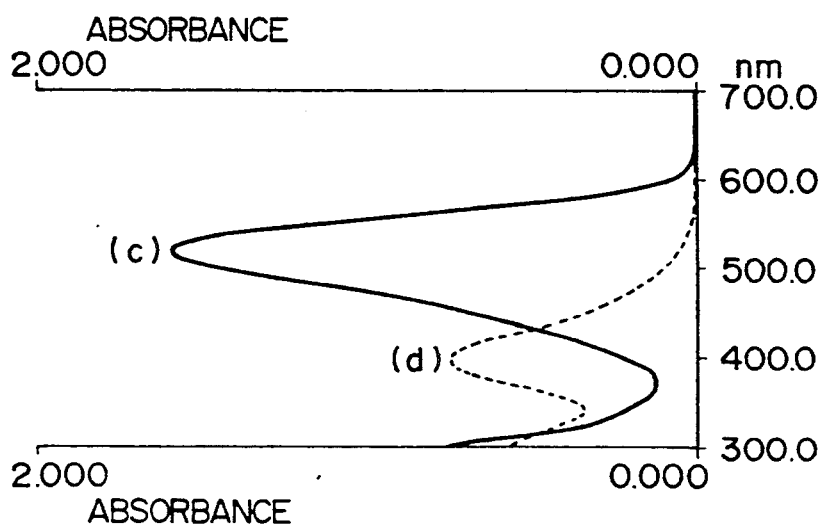
FIG. 2 shows UV spectra of (c) sodium 4-phenylaza-1-naphthol-4'-sulfonate and (d) 4-(4'-sulfophenylazo)-1-naphthyl-N-acetyl-β-D-g lucosaminde sodium salt.

FIG. 1 shows UV spectra of (a) sodium-4-phenylazo-1-naphthol-4'-nitro-2'-sulfonate (phenylazonaphthol derivative: dye) and (b) 4-(4'-nitro-2'-sulfophenylazo)--naphthyl-N-acetyl-β-D-glucosaminide sodium salt (substrate). FIG. 2 shows UV spectra of (c) sodium 4-phenylazo-1-naphthol-4'-sulfonate (phenylazonaphthol derivative: dye) and (d) 4-(4'-sulfophenylazo)-1-naphthyl-N-acetyl-β-D-glucosaminide sodium salt (substrate). As is evident from FIGS. 1 and 2, at wavelengths showing the absorption peaks of dyes (a) and (C), absorptions of the substrates (b) and (d) corresponding to the dyes are extremely weak.

These substrates can by synthesized according to the following reaction equation. That is, N-acetyl glucosamine is acetylated. After the acetylated N-acetylglucosamine is bound to the substituted aromatic compounds, aglycons, deacetylation is performed (Lecture on Experimental Chemistry, 24, 304, 1958). Alternatively, the acetylated N-acetylglycosamine is halogenated and the halogenated product is bound to the substituted aromatic compounds, aglycons, through ether bond followed by acetylation (Methods in Carbohydrate Chemistry, II, 334).

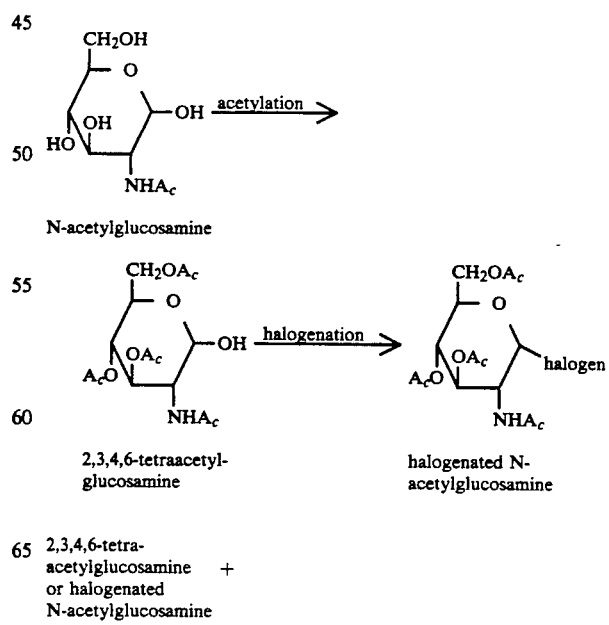

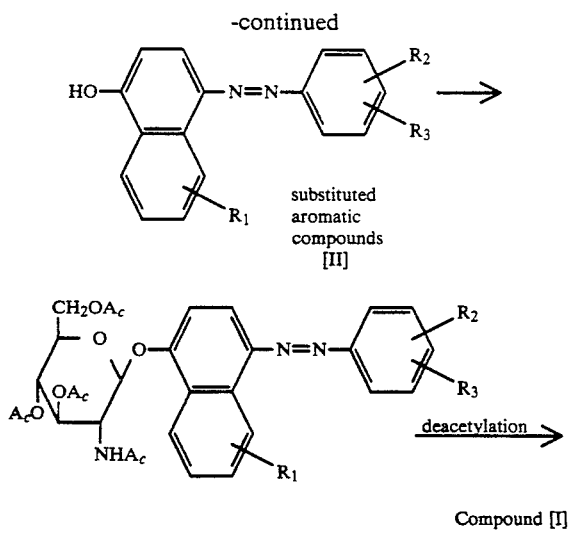

The buffer solution which can be used in the reagent for determining NAG activity of the present invention may be any buffer solution so long as it can maintain the optimum pH, 4.0 to 6.0, NAG in a sample. Examples of the buffer solution include citrate buffer solution and other organic acid buffer solutions. The buffer solution may also contain a surface active agent, a preservative, sodium chloride, a stabilizer, etc., if necessary and desired.

As stated above, the present invention enables to determine NAG activity. In more detail, the NAG activity in a sample can be determined by incubating NAG in a sample and phenylnaphthyl-N-acetyl-β-D-glucosaminide glucosaminide derivative as its substrate to perform enzyme reaction, allowing the released phenylazonaphthol derivative to form a color with an alkali solution and colormetrically determining the color.

As the alkali solution, any alkali solution is usable inasmuch as it can render the system alkaline property sufficient to form a detectable color of the released phenylazonaphthol derivative through formation of an azo dye. The colorimetry utilizing the azo dye formation is well known in the art and no further explanation is believed necessary. In view of the assay system involved in the present invention, however, it is preferred to adjust the pH to a range of from about 9 to about 11.

The determination of the present invention can be any of the rate assay and the endpoint assay. That is, the NAG activity can be determined either by the rate assay in which a difference in absorbance is measured as with passage of time in a definite time during which the enzyme reaction proceeds, or by the endpoint assay wherein a reaction terminating solution is added. In addition, the absorption wavelength of the released phenylazonaphthol derivative lies between 500 and 600 nm which are hardly affected by contaminants in a vital sample upon determination. Therefore, accurate measurement results can be obtained using the reagent of the present invention for determining NAG activity.

Furthermore, as is clear from FIGS. 1 and 2, the absorptions of substrates (b) and (d) are extremely weak at wavelengths showing the absorption peaks of dyes (a) and (c). Thus, when the reaction can be traced at the wavelengths showing the absorption peaks, the reduction in substrate can be accurately traced.

Hereafter the present invention is described in more detail, by referring the examples and test examples but is not deemed to be limited thereto.

EXAMPLE 1

Synthesis of 4-(4'-nitro-2'-sulfophenylazo)-1-naphthyl-N-acetyl-β-D-glucosaminide sodium salt (a) A solution of 9.3 g (25.3 mmols) of 2,3,4,6-tetraacetylglucosamine chloride in 75 ml of chloroform was heated to 60° C. At this temperature, a solution of 3.4 g (12.6 mmols) of triethylbenzylammonium chloride and 5.0 g (12.6 mmols) of 4-(4'-nitro-2'-sulfophenylazo)-1-naphthol in 25.3 ml of 1 N soldium hydroxide was added to the solution. The reaction mixture was refluxed for 6 hours and then stirred at room temperature overnight. The organic phase was separated and the aqueous phase was shaken with chloroform several times. The combined organic phases were shaken with 0.1 N sodium hydroxide aqueous solution to remove the starting material. After the chloroform phase was washed with water and dried over magnesium sulfate, the organic solvent was concentrated. The residue was dropped onto ether to give 2.8 g of 4-(4'-nitro-2'-sulfophenylazo)-1-naphthyl-2,3,4,6-tetraacetylglucosaminide sodium salt.

Red amorphous powder (yield: 31% of the theoretical amount)

Silica gel thin layer chromatography (developing solvent, n-butyl alcohol: acetic acid : water =4:1:1 v/v): Rf =0.78

(b) A solution of 2.8 g (3.9 mmols) of the tetraacetyl-glucosaminide obtained in (a) in 20 ml of absolute methanol was cooled to 0 to 5° C. For deacetylation, 0.46 ml (2 mmols) of 28% sodium methylate solution in methanol was added to the solution at the same temperature. After stirring at 0 5° C. for an hour, the reaction mixture was poured onto 500 ml of dry ether to precipitate the product. After the product was taken by filtration, washed with ether and then dried under reduced pressure, the product was purified by column chromatography to give 0.7 g of 4-(4'-nitro-2'-sulfophenylazo)-1-naphthyl-N-acetyl-β-D-glucosaminide sodium salt.

Red amorphous powder (yield: 16& of the theoretical amount)

Melting point: 120–124° C. (decomposed)

Silica gel thin layer chromatography (developing solvent, n-butyl alcohol : acetic acid : water =4:1:1 v/v): Rf =0.32

EXAMPLE 2

The corresponding substrates were synthesized by reacting the phenylazonaphthol derivatives described below with tetraacetylglucosaminide chloride in a manner similar to Example 1.

| Starting Material | Physical properties of Substrates obtained | |
|---|---|---|
| | Rf value | Melting point (°C.) |
| 4-phenylazo-1-naphthol-4'-sulfonic acid | 0.22 | 160–164 |
| 4-(4'-Nitrophenylazo)-1-naphthol-5-sulfonic acid | 0.26 | 150–155 |
| 4-(4'-Nitrophenylazo)-1-naphthol-8-sulfonic acid | 0.28 | 88–92 |
| 4-Phenylazo-1-naphthol- | 0.29 | 98–102 |

-continued

| | Physical properties of Substrates obtained | |
|---|---|---|
| Starting Material | Rf value | Melting point (°C.) |
| 5-sulfonic acid | | |

(The developing solvent for thin layer chromatography is the same as in Example 1)

TEST EXAMPLE 1

Determination of Enzyme Activity (a) Preparation of solutions used

| Buffer solution: | |
|---|---|
| Citric acid | 25 mM aqueous solution |
| Sodium citrate | 25 mM aqueous solution |

The above-mentioned two solutions were mixed and the pH was adjusted to 4.2.

Reagent solution 1

4-(4'-Nitro-2'-sulfophenylazo)-1-naphthyl-N-acetyl-$\beta$-D-glucosaminide sodium salt was dissolved in the buffer solution in a concentration of 0.5 mM.

Reagent solution 2

| Diethanolamine | 1 M |
| Magnesium chloride | 0.5 mM |
| pH (adjusted with hydrochloric acid) | 10.5 (25° C.) |

Enzyme solution

Commercially available NAG was dissolved in the buffer solution. The activity of the solution was about 100 U/l (b) Method The NAG activity was determined by the endpoint assay. After 1 ml of the reagent solution 1 was taken and heated at 37° C. for 5 minutes, 0.1 ml of the enzyme solution was added to and mixed with the reagent solution 1. After reacting at 37° C. for 5 minutes, 2 ml of the reagent solution 2 was added to terminate the reaction. After settling for 5 minutes, the absorbance was measured at 600 nm (for substrate blank, water was used instead of the enzyme solution).

The enzyme solution was serially diluted with physiological saline in 10 levels. The measurement data are shown below.

| Dilution Rate | OD Value (− Blank) |
|---|---|
| 1/1 | 0.036 |
| 2/10 | 0.074 |
| 3/10 | 0.105 |
| 4/10 | 0.150 |
| 5/10 | 0.176 |
| 6/10 | 0.226 |
| 7/10 | 0.251 |
| 8/10 | 0.287 |
| 9/10 | 0.324 |
| 10/10 | 0.375 |

Figure 3:
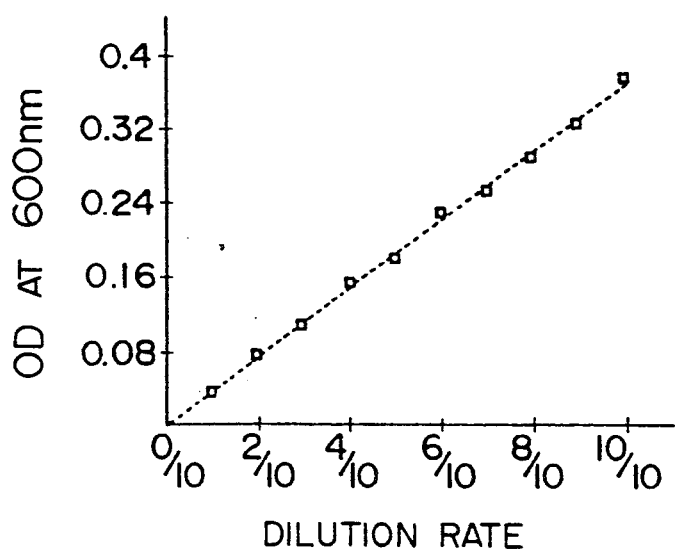
FIG. 3 is a graph showing relationship between diluted NAG and optical density (OD).

FIG. 3 is a graph showing relationship between diluted NAG and OD. The results indicate a good straight line passing the origin. The fact indicates that the NAG activity is in a relation proportional to OD. The results also show the practicability and usefulness of the new method for determination of NAG activity.

TEST EXAMPLE 2

Determination of enzyme activity (A) Preparation of solutions used.

| Buffer solution: | |
|---|---|
| Citric acid | 50 mM aqueous solution |
| Sodium citrate | 50 mM aqueous solution |

The above-mentioned solutions were mixed and the pH was adjusted to 5.0.

Reagent solution 4-(4'-Sulfophenylazo)-1-naphthyl-N-acetyl-$\beta$-D-glucosaminide sodium salt was dissolved in water in a concentration of 2 mM.

Enzyme solution

Commercially available NAG was dissolved in the buffer solution. The activity of the solution was about 200 U/l.

(b) Method

The NAG activity was determined by the rate assay. After 1.5 ml of the buffer solution and 0.2 ml of the reagent solution were taken and heated at 37° C. for 30 seconds 25 $\mu$l of the enzyme solution was added to the mixture. After stirring, an increase in absorbance at 505 nm was measured with a spectrophotometer.

The enzyme solution was serially diluted with physiological saline in 5 levels. The measurement data are shown below.

| Dilution Rate | $\Delta$OD Value (10 mins.) |
|---|---|
| 0/5 | 0.0004 |
| 1/5 | 0.0786 |
| 2/5 | 0.1428 |
| 3/5 | 0.2036 |
| 4/5 | 0.2746 |
| 5/5 | 0.3421 |

Figure 4:
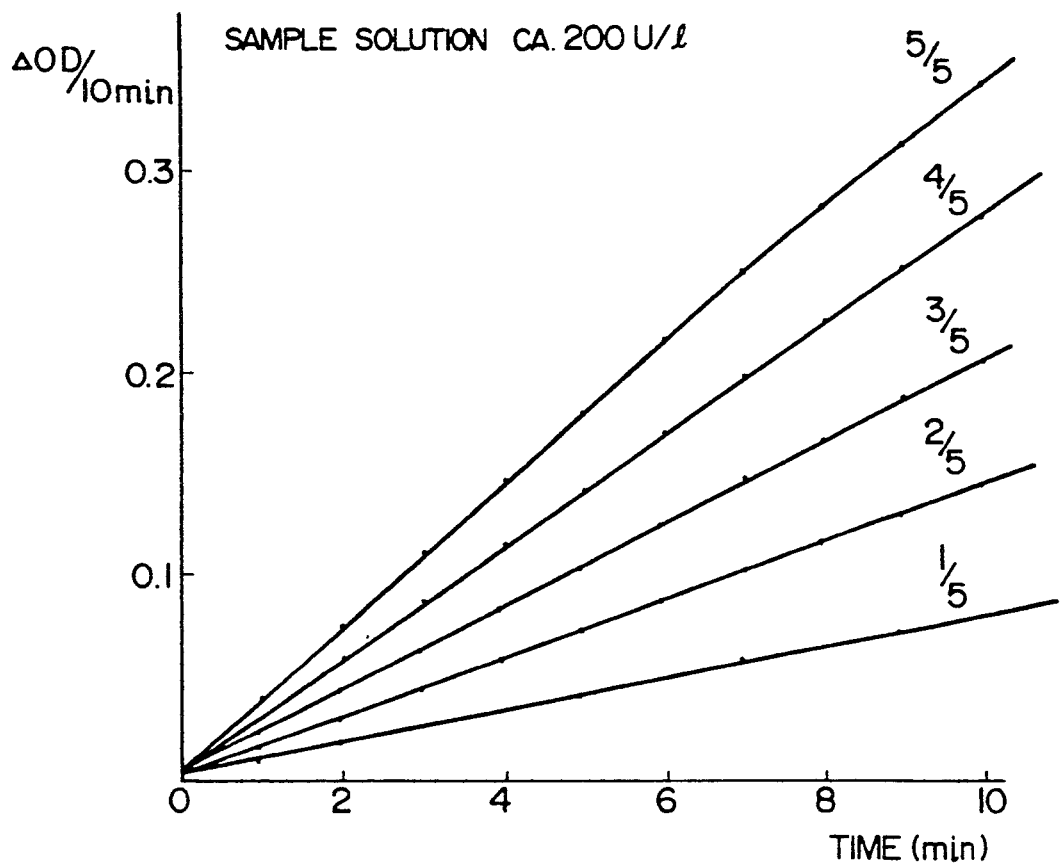
FIG. 4 shows a time course by diluted NAG.

FIG. 4 shows the results obtained measuring a time course by diluted NAG twice. As is noted from FIG. 4, 5/5 showed linearity up to 8 minutes and other NAG samples showed linearity up to 10 minutes. The results indicate that the rate assay is applicable at least up to 200 U/l.

Figure 5:
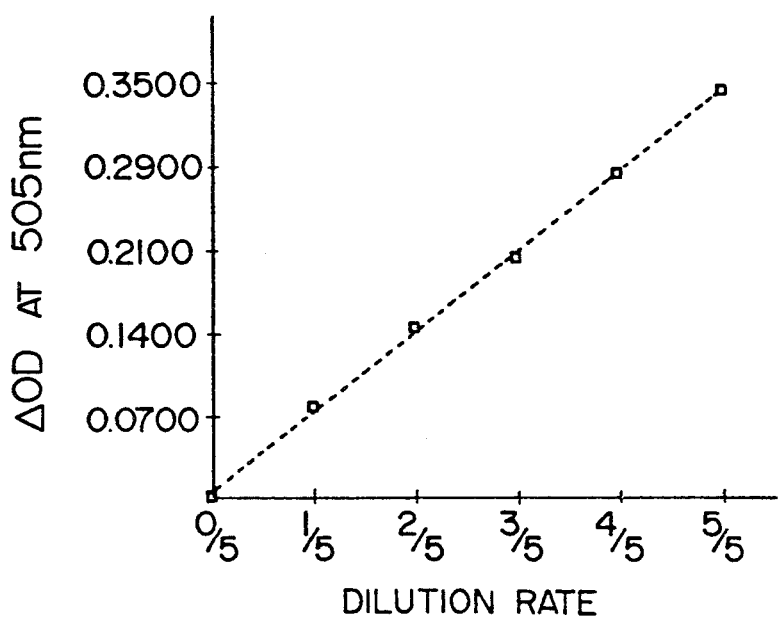
FIG. 5 is a graph showing relationship between diluted NAG and ΔOD.

FIG. 5 is a graph showing relationship between diluted NAG and $\Delta$OD. The results indicate a good straight line passing the origin. This fact shows that the NAG activity is in a relation proportional to $\Delta$OD and at the same time, shows the practicability and usefulness of the new method for determination of NAG activity.

According to the method for determination of NAG activity of the present invention, the problems in the conventional methods are solved in various aspects. The advantages of the present invention are summarized below.

(1) The substrate is readily soluble in water so that the substrate can be set in any desired concentration in the reaction solution so that the reaction can be performed without being affected by interferents in urine.

(2) Wavelengths for measurement are set forth in a range of 500 to 600 nm and the measurement is hardly affected by contaminants in a vital sample. Therefore, it can be omitted to measure a sample blank. For this reason, accurate measurement results can be obtained.

(3) Since the azo dye having a relatively large molecular extinction coefficient is used as a coloring substance, the measurement is possible even in a short period of time.

(4) Depending upon kind of dye used, not only the endpoint assay but also the rate assay can be performed.

As described above, the method for determination of NAG activity according to the present invention can solve the problems encountered in the prior art and enables to accurately determine NAG activity in a simple way.

Therefore, the method for determination of NAG activity of the present invention is extremely useful for determining NAG activity in urine collected from normal volunteers, patients with renal disorders, etc.

What is claimed is:

1. A phenylazonaphthyl-N-acetyl-$\beta$-D-glucosaminide derivative represented by formula:

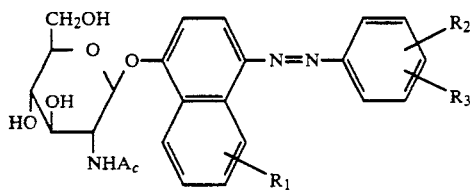

wherein $R_1$, $R_2$, and $R_3$ are independently selected from a sulfonic acid group, an alkali metal sulfonate group, a halogen atom, a methoxy group, a nitro group or a hydrogen atom; provided, however, that at least one of the aforesaid R groups is a sulfonic acid group or an alkali metal sulfonate group.

2. A phenylazonaphthyl-N-acetyl-$\beta$-D-glucosaminide derivative as claimed in claim 1, wherein said alkali metal sulfonate group is selected from sodium sulfonate and potassium sulfonate.

3. A phenylazonaphthyl-N-acetyl-$\beta$-D-glucosaminide derivative as claimed in claim 1, wherein said halogen atom is selected from chlorine, bromine and iodine.

4. A phenylazonaphthyl-N-acetyl-$\beta$-D-glucosaminide derivative of claim 1, which is selected from 4-phenylazo-1-naphthol-4'-sulfonic acid, 4-phenylazo-1-naphthol-4'-nitro-2'-sulfonic acid, 4-(4'-methoxyphenylazo)-1-naphthol-5-sulfonic acid and 4-(2'-chloro-4'-nitro-phenylazo)-1-naphthol-5-sulfonic acid and alkali metal salts thereof.

5. A reagent for determining N-acetyl-$\beta$-D-glucosaminidase activity containing a buffer and as substrate a phenylazonaphthyl-N-acetyl-$\beta$-N-glucosaminide derivative represented by formula:

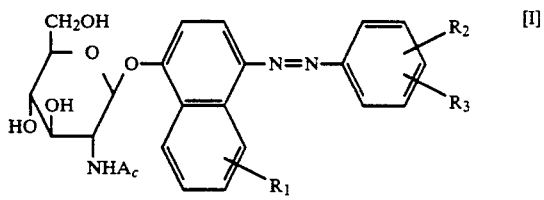

wherein Rphd 1, $R_2$, and $R_3$ are independently selected from a sulfonic acid group, an alkali metal sulfonate group, a halogen atom, a methoxy group, nitro group or a hydrogen atom; provided, however, that at least one of the aforesaid R groups is a sulfonic acid group or an alkali metal sulfonate group.

6. A reagent for determining N-acetyl-$\beta$-D-glucosaminidase activity as claimed in claim 5, wherein said alkali metal sulfonate group is selected from sodium sulfonate and potassium sulfonate.

7. A reagent for determining N-acetyl-$\beta$-D-glucosaminidase activity as claimed in claim 5, wherein said halogen atom is selected from chlorine, bromine and iodine.

8. A reagent for determining N-acetyl-$\beta$-D-glucosaminidase activity of claim 5, wherein said phenylazonaphthol derivative is selected from 4-phenylazo-1-naphthol-4'-sulfonic acid, 4-phenylazo-1-naphthol-4'-sulfonic acid, 4-phenylazo-1-naphthol-4'-sulfonic acid, 4-(4'-methoxyphenylazo)-1-naphthol-5-sulfonic acid and 4-(2'-chloro-4'-nitrophenylazo)-1-naphthol-5-sulfonic acid and alkali metal salts thereof.

* * * * *